United States Patent
Gregoris

(10) Patent No.: US 10,517,801 B2
(45) Date of Patent: Dec. 31, 2019

(54) METHOD TO PREPARE A CREAM PRODUCT

(71) Applicant: BAKEL S.R.L., Udine (IT)

(72) Inventor: Raffaella Gregoris, Udine (IT)

(73) Assignee: BAKEL S.R.L., Udine (IT)

( * ) Notice: Subject to any disclaimer, the term of this patent is extended or adjusted under 35 U.S.C. 154(b) by 0 days.

(21) Appl. No.: 15/767,693

(22) PCT Filed: Oct. 13, 2016

(86) PCT No.: PCT/IB2016/056137
§ 371 (c)(1),
(2) Date: Apr. 12, 2018

(87) PCT Pub. No.: WO2017/064644
PCT Pub. Date: Apr. 20, 2017

(65) Prior Publication Data
US 2018/0289596 A1    Oct. 11, 2018

(30) Foreign Application Priority Data

Oct. 13, 2015 (IT) .......................... 102015000061238

(51) Int. Cl.
*A61K 8/06* (2006.01)
*A61Q 19/00* (2006.01)
*A61K 8/92* (2006.01)

(52) U.S. Cl.
CPC .............. *A61K 8/062* (2013.01); *A61K 8/922* (2013.01); *A61Q 19/00* (2013.01); *A61K 2800/805* (2013.01)

(58) Field of Classification Search
None
See application file for complete search history.

(56) References Cited

U.S. PATENT DOCUMENTS

| 4,684,522 A * | 8/1987 | Marissal | A61K 8/585 424/401 |
| 2003/0032680 A1* | 2/2003 | Singh | A61K 8/06 516/38 |
| 2004/0116539 A1* | 6/2004 | Biercevicz | B01F 3/04985 516/21 |
| 2007/0292461 A1* | 12/2007 | Tamarkin | A61K 8/86 424/401 |
| 2013/0071346 A1* | 3/2013 | Okada | A61Q 5/12 424/70.27 |
| 2013/0331468 A1* | 12/2013 | Uyama | A61K 8/042 514/786 |

FOREIGN PATENT DOCUMENTS

| EP | 0134483 | * | 3/1985 |
| EP | 2682094 | | 1/2014 |
| EP | 2755627 | | 7/2014 |
| FR | 3019741 | * | 10/2015 |
| WO | 2004054693 | | 7/2004 |

OTHER PUBLICATIONS

Definition of Stir, Dictionary.com, retrieved online on Mar. 6, 2019 (Year: 2019).*
International Search Report filed in PCT/IB2016/056137 dated Oct. 1, 2017.

* cited by examiner

*Primary Examiner* — Jennifer A Berrios
(74) *Attorney, Agent, or Firm* — Rankin, Hill & Clark LLP

(57) ABSTRACT

A method to prepare a cream product includes separately preparing an exclusively aqueous phase and a mixed fatty/aqueous phase, and assembling and emulsify the exclusively aqueous phase and the mixed fatty/aqueous phase.

9 Claims, No Drawings

METHOD TO PREPARE A CREAM PRODUCT

FIELD OF THE INVENTION

Embodiments described here concern a method to prepare a cream product, in particular a cream product usable as a cosmetic composition, for treating or caring for the skin.

Hereafter, without limiting the present invention, by cream product we mean an ointment, or spreadable cosmetic pastes in general, obtained in the form of an emulsion.

BACKGROUND OF THE INVENTION

As spreadable cosmetic compositions, such as cream, or as cosmetic compositions left on the skin, it is known to use oil in water emulsions, that is, emulsions in which the fatty phase or component is dispersed in the aqueous phase or component.

The fatty phase, due to its affinity with the skin, facilitates the application of the composition.

Typically, an oil in water emulsion tends of itself to be instable and, for the purposes of stability, the correct homogenization of the individual aqueous and fatty phases plays a fundamental role; the correct stabilization of the two phases is also important. Otherwise, there would be a breakage of the emulsion, that is, the separation of the aqueous phase from the fatty phase. For practical purposes, this would cause for the final consumer an unpleasant appearance and sensation on the skin, which would obviously lead to a limited commercial success of a product of the type in question and also a limited efficaciousness thereof.

Other limitations and disadvantages of conventional solutions and technologies will be clear to a person of skill after reading the remaining part of the present description with reference to the description of the embodiments that follow, although it is clear that the description of the state of the art connected to the present description must not be considered an admission that what is described here is already known from the state of the prior art.

There is therefore a need to perfect a method to prepare a cream product which can overcome at least one of the disadvantages of the state of the art.

In particular, one purpose of the present invention is to perfect a method to prepare a cream product, in the form of an oil in water emulsion, which guarantees an adequate homogenization of the fatty phase in the aqueous phase without risking a separation of the two phases and thus compromising the integrity of the cream.

Another purpose of the present invention is to provide a method to prepare a cream product with a formula that consists exclusively of compounds functional for the skin and/or compounds functional both for the skin and also for the structure of the formula, and which does not comprise compounds exclusively functional for the structure of the formula.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, embodiments described here concern a method to prepare a cream product.

According to one aspect of the present invention, the method to prepare a cream product provides to:
  separately prepare an exclusively aqueous phase, assembling water-soluble compounds in hot conditions and a first portion of water, and a mixed fatty/aqueous phase, assembling in hot conditions a fatty phase of lipid-soluble compounds and adding to the fatty phase a second portion of water;
  assemble, and emulsify by stirring, the exclusively aqueous phase and the mixed fatty/aqueous phase.

Advantageously, the preparation method is particularly indicated for the production of a cream product whose formula provides compounds at least functional for the skin and possibly functional also for the structure of the formula.

These and other aspects, characteristics and advantages of the present disclosure will be better understood with reference to the following description and attached claims.

The various aspects and characteristics described in the present description can be applied individually where possible. These individual aspects, for example aspects and characteristics described in the description or in the attached dependent claims, can be the object of divisional applications.

It is understood that any aspect or characteristic that is discovered, during the patenting process, to be already known, shall not be claimed and shall be the object of a disclaimer.

DETAILED DESCRIPTION OF SOME EMBODIMENTS

We shall now refer in detail to the various embodiments of the present invention. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

All the measurements, except when indicated to the contrary, are carried out at 25° and at atmospheric pressure. All the temperatures, unless otherwise indicated, are expressed in degrees Celsius.

All the percentages and ratios indicated are understood as referred to the weight of the whole composition (w/w), unless otherwise indicated.

All the percentage ranges reported here are supplied with the proviso that the sum with respect to the overall composition is 100%, unless otherwise indicated.

All the ranges reported here are understood to include the extremes, including those that report a range "between" two values, unless otherwise indicated.

The ranges that derive from the overlapping or union of two or more ranges described are also included in the present description, unless otherwise indicated.

The ranges that can derive from the combination of two or more time values described are also included in the present description, unless otherwise indicated.

Terms such as "about", "generally", "substantially" and suchlike shall be understood with their function of modifying a term or value that is not absolute, but is not reported in the state of the art. Such terms shall be defined by the specific circumstances and by the terms that they are intended to modify according to the common acceptance of such terms in the specific field. They shall take into account at least the degree of experimental error expected, the technical error and the instrumental error for a given technique adopted to measure a value. Unless otherwise indicated, in the present description, singular forms such as "a", "an" and "one" shall be understood to include plural forms, unless the context suggests otherwise.

Embodiments described here concern a method to prepare a cream product that provides to separately prepare an exclusively aqueous phase and a mixed fatty/aqueous phase, for example using two separate turbo-emulsifiers, assembling water-soluble compounds in hot conditions and a fatty phase of lipid-soluble compounds respectively of the exclusively aqueous phase and the mixed fatty/aqueous phase. In particular the two phases, aqueous and mixed fatty/aqueous, are stirred separately, in order to obtain the homogenisation in hot conditions of the components, and once they have been homogenized in hot conditions, and separately, the mixed fatty/aqueous phase is added, that is dispersed, in the exclusively aqueous phase.

Here and hereafter, in order to indicate the exclusively aqueous phase the expression "aqueous" could be used, to indicate a phase containing water and possible water-soluble compounds.

Therefore, embodiments described here differ from the state of the art in the hot preparation of the exclusively aqueous phase and the mixed fatty/aqueous phase separately and the subsequent addition of the mixed fatty/aqueous phase in the exclusively aqueous phase, obtaining the emulsion.

In embodiments of the method in accordance with the present description, for the preparation of each phase, exclusively aqueous or mixed fatty/aqueous, an appropriate turbo-emulsifier can be used. A turbo-emulsifier is a mixer provided with a stirrer and a heat exchange device, which can be used to heat the specific phase to be worked, and also to cool it, when required. Moreover, the turbo-emulsifier is able to operate in vacuum conditions.

In particular, the stirrer can typically be a planetary stirrer ("planet"), for example with anchors and blades, for example with three blades.

The anchors, for example, are provided with scrapers, while the blades are coaxial to the anchors, counter-rotating thereto and determining a horizontal mixing.

Moreover, the turbo-emulsifier can also be provided with a high speed stirrer attached in correspondence to the lid and coaxial to the stirrer and to the counter-rotating blades. In this way, the combination of anchors and blades allows to obtain a vertical and horizontal mixing, as well as a cutting action useful for the mixing of semi-worked products which are particularly viscous.

Moreover, the heat exchange device of the turbo-emulsifier can be provided with a heat exchange jacket, in which a heating fluid can be made to flow and, if necessary, also to cool. The turbo-emulsifier can also be provided with a turbine and a suction pump to create a vacuum condition ("airless" function).

In accordance with a possible embodiment, in a first operating step the method provides to load a first portion of water in a first turbo-emulsifier, to start the stirring and to heat it to a temperature for example between 45° C. and 55° C., in particular between 48° C. and 52° C.

In one embodiment, the first portion of water goes from 65% w/w to 75% w/w, in particular from 67% w/w to 73% w/w with respect to the total quantity of water present in the formula of the final cream product discussed here.

In some embodiments, combinable with all the embodiments described here, the water is the sterilized and demineralized type, advantageously obtained without the addition of chemical products, for example using ultraviolet rays and an electronic control of the electric conductivity using a microprocessor.

In particular, the heating of the first portion of water can be carried out using steam generated by heaters located externally to the building and which is brought into the jacket of the first turbo-emulsifier. Once the heating has finished, the steam exits from the turbo-emulsifier in the form of condensation which is returned to the heaters.

Once a temperature between 35° C. and 45° C. has been reached, in particular between 38° C. and 42° C., possible water-soluble compounds required by the specific formula of the cream product to be prepared can be added to the first portion of water present in the first turbo-emulsifier. The addition of these possible water-soluble compounds to the exclusively aqueous phase in practice entails the formation of an aqueous solution.

In one embodiment, the water-soluble compounds are added to the first portion of water starting from a water-soluble compound present in greater percentages of weight (w/w %) to then add in scalar manner the water-soluble compounds progressively present with slightly lower percentages in weight.

In accordance with a possible embodiment, the method in a second operating step provides to load the whole quantity of fatty phase provided by the specific formula of the cream product to be prepared in a second turbo-emulsifier, to start the stirring and to heat it, in order to melt it, using steam for example, in order to reach a temperature between 45° C. and 55° C., in particular between 48° C. and 52° C. For example, the stirrer of the second turbo-emulsifier can be specifically configured to stir the fatty compounds in the melting step, for example vegetable oils, vegetable butters, waxes, or other lipid-soluble compounds suitable for cream products in question.

Once the fatty phase has been completely melted, a second portion of water previously heated to a temperature substantially equal to the temperature of the fatty phase, for example between 45° C. and 55° C., in particular between 48° C. and 52° C. This second portion of water, added to said first portion of water, represents the total portion of water present and required in the formula of the final cream product in question.

In one embodiment, the first portion of water comprised in the exclusively aqueous phase is greater in percentage of weight with respect to the second portion of water added to the fatty phase.

In particular, the second portion of water goes from 25% to 35% w/w, in particular from 27% w/w to 33% w/w, with respect to the total quantity of water present in the formula of the final cream product.

The added mass of fatty phase of the second portion of water, that is, the mixed fatty/aqueous phase, is stirred for example for between 24 minutes and 36 minutes, in particular between 27 minutes and 33 minutes, at a speed that goes from 2,500 rpm to 3,500 rpm, in particular from 2,800 rpm to 3,200 rpm, keeping it at the same temperature.

In the embodiments where they are provided, the anchors of the planet stirrer scrape the wall of the turbo-emulsifier, taking the semi-worked product upward, and the blades, more internal and located at a different height, on the contrary take the semi-worked product downward. This allows an effective homogenization of the mass of mixed fatty/aqueous phase.

When the stirring time has finished, the stirring speed is reduced to a speed comprised between 490 rpm and 510 rpm, in particular between 495 rpm and 505 rpm, until a temperature between 35° C. and 45° C. is reached, in particular between 38° C. and 42° C.

The homogenized mass of mixed fatty/aqueous phase present in the second turbo-emulsifier is introduced, in particular poured, into the first turbo-emulsifier where there is the exclusively aqueous phase. The introduction can be made by means of a tube which can have a filter.

In possible embodiments, the suction pump associated with the turbo-emulsifier can be activated to create a vacuum so as not to incorporate air during stirring and subsequent homogenization, to prevent the semi-worked product from being "swollen", and hence not very pleasant.

At this point, the total mass present in the first turbo-emulsifier is stirred, with a stirring speed comprised between 2,500 rpm and 3,500 rpm, in particular between 2,800 rpm and 3,200 rpm, at a temperature between 45° C. and 55° C., in particular between 48° C. and 52° C., to refine and homogenize the particles of the mass more finely, for the purposes of emulsification. In this way, the mixed fatty/aqueous phase emulsifies effectively with the exclusively aqueous phase.

In possible embodiments, after stirring, the compound in emulsion now present in the first turbo-emulsifier can also be subjected to filtering. To this purpose, in possible implementations, the emulsion compound obtained in the first turbo-emulsifier is again introduced, in particular poured, into the second turbo-emulsifier, and is made to pass through a sieve filter, for example at 10 μm, at a pressure between 0.6 bar and 1.3 bar, in particular between 0.8 bar and 1.2 bar.

At this point, the emulsion compound in the second turbo-emulsifier is cooled quickly to a temperature comprised between 15° C. and 25° C., in particular between 18° C. and 22° C., by introducing cooling water into the heat exchange device of the second turbo-emulsifier.

When emulsion and homogenization are complete, the compound thus cooled and obtained assembling and emulsifying the exclusively aqueous phase and the mixed fatty/aqueous phase through stirring, can be transferred into suitable containers, and then left to rest.

In particular, the cooled compound in the second turbo-emulsifier is left to rest for at least 24 hours, to prevent a possible separation of the fatty phase from the aqueous phase.

Furthermore, in some embodiments, after the resting phase of 24 hours, the compound can be heated inside the turbo-emulsifier to a temperature between 30° C. and 40° C., in particular between 43° C. and 48° C., and kept slowly stirred between 100 rpm and 200 rpm, in particular between 130 rpm and 170 rpm, to add possible additional compounds functional for the structure of the composition and/or for the skin. In this case too, the final product is left to rest.

During the resting phase it is possible to perform chemical-physical controls on the cream product, such as controls on the pH, viscosity, specific weight, and microbiological controls, such as a control on the microbe load, search for pathogens if necessary.

In some embodiments, the cream product can be a cream for treating the skin, a body cream, a face cream, a hand cream, a leg cream, a foot cream, a hair cream, an emollient balsam cream for the hair, a cream for around the eyes or for the eyelids.

The preparation method according to the embodiments described here, in particular thanks to the initial preparation of the two phases, mixed fatty/aqueous phase and exclusively aqueous phase, in two different turbo-emulsifiers, provides to obtain cream products formed from emulsions that cover a wide range of viscosity, from fluid emulsions, usually with a viscosity with about 2,000 cps, and pasty emulsions, usually with a viscosity of about 80,000 cps, both measured at 25° C. with a rotational viscometer, for example made by Fungilab, model Visco Star +R, Alpha series, or Alpha.

The present invention is advantageously suitable for the preparation of cream products of the type described in the Italian patent application n. 102015000034711, the formula of which consists exclusively of compounds functional for the skin and/or compounds functional both for the skin and also for the structure of the formula.

Therefore, embodiments of the method described here provide that the water-soluble compounds present in the exclusively aqueous phase and the lipid-soluble compounds of the fatty phase, together with the water present, define the formula of the cream product itself, and that this formula, as described above, consists exclusively of compounds functional for the skin and/or compounds functional both for the skin and also for the structure of the formula.

Therefore, the cream products do not comprise compounds exclusively functional for the structure of the formula.

A cream product with these characteristics, to have cross-linking properties and to obtain a certain texture, needs a particular production method which the present invention allows to obtain.

Therefore, the separate preparation, which can advantageously provide to use two separate and distinct turbo-emulsifiers, of the exclusively aqueous phase and the mixed fatty/aqueous phase, allows to obtain a stable emulsion, unlike known production methods which provide to add the compounds both of the fatty phase and also of the aqueous phase on each occasion in a single turbo-emulsifier.

It is clear that modifications and/or additions of parts may be made to the method to prepare a cream product as described heretofore, without departing from the field and scope of the present invention.

It is also clear that, although the present invention has been described with reference to some specific examples, a person of skill in the art shall certainly be able to achieve many other equivalent forms of method to prepare a cream product, having the characteristics as set forth in the claims and hence all coming within the field of protection defined thereby.

The invention claimed is:

1. A method to prepare a cream product, comprising:
separately preparing an exclusively aqueous phase and a mixed fatty/aqueous phase, the exclusively aqueous phase being prepared by assembling water-soluble compounds in hot conditions and a first portion of water, and the mixed fatty/aqueous phase being prepared by assembling in hot conditions a fatty phase of lipid-soluble compounds and adding to said fatty phase a second portion of water; and
assembling and emulsifying by stirring the exclusively aqueous phase and the mixed fatty/aqueous phase,
wherein a first operating step of said method includes loading said first portion of water in a first mixer provided with a stirrer and a heat exchange device, stirring and heating the first portion of water to a temperature between 45° C. and 55° C., once a temperature of the first portion of water is between 35° C. and 45° C., adding said water-soluble compounds to said first portion of water present in the first mixer, then heating the water-soluble compounds and the first portion of water to a temperature between 45° C. and 55° C. to obtain said exclusively aqueous phase;

wherein a second operating step of said method includes providing the fatty phase in an entire quantity to be included in the cream product as specified by a specific formula of the cream product, loading the fatty phase in a second mixer provided with a stirrer and a heat exchange device, stirring and heating the fatty phase to reach a temperature between 45° C. and 55° C. and thereby melting said fatty phase, once the fatty phase has been completely melted, adding said second portion of water, which has been previously heated to a temperature equal to the temperature of the fatty phase, to the second mixer and stirring the fatty phase and the second portion of water to thereby obtain a homogenized mass of the mixed fatty/aqueous phase in the second mixer; and wherein a third operating step of said method includes introducing the mixed fatty/aqueous phase into the first mixer and emulsifying the mixed fatty/aqueous phase with the exclusively aqueous phase in the first mixer at a temperature between 45° C. and 55° C.

2. The method as in claim 1, wherein preparing said exclusively aqueous phase and said mixed fatty/aqueous phase includes stirring separately the exclusively aqueous phase and the mixed fatty/aqueous phase, and obtaining a homogenization of components in hot conditions.

3. The method as in claim 1, wherein said first portion of water is bigger than said second portion of water added to the fatty phase, in a percentage of weight with respect to the formula of a final cream product.

4. The method as in claim 3, wherein the first portion of water goes from 65% w/w to 75% w/w with respect to a total quantity of water present in the formula of the final cream product.

5. The method as in claim 3 wherein said second portion of water goes from 25% w/w to 35% w/w with respect to the total quantity of water present in the formula of the final cream product.

6. The method as in claim 1, wherein assembling said water-soluble compounds further includes adding into said first portion of water starting from a respective water-soluble compound present in the greatest percentage of weight (w/w %) and then progressively adding remaining water-soluble compounds present with gradually lower percentages of weight in scalar manner.

7. The method as in claim 1, further comprising obtaining cream products formed by emulsions in a range of viscosity from about 2 Pa•s (2,000 cps) to about 80 Pa•s (80,000 cps), measured at 25° C. with a rotational viscometer.

8. The method as in claim 1, wherein the water is sterilized and demineralized.

9. The method as in claim 1, wherein the cream product obtained when assembling and emulsifying by stirring the exclusively aqueous phase and the mixed fatty/aqueous phase is left to rest.

* * * * *